United States Patent [19]

Swartz et al.

[11] Patent Number: 5,269,302
[45] Date of Patent: Dec. 14, 1993

[54] ELECTROCONVULSIVE THERAPY APPARATUS AND METHOD FOR MONITORING PATIENT SEIZURES

[75] Inventors: Conrad M. Swartz, Norman, Okla.; Richard S. Abrams, Vernon Hills, Ill.

[73] Assignee: Somatics, Inc., Lake Bluff, Ill.

[21] Appl. No.: 876,710

[22] Filed: May 6, 1992

Related U.S. Application Data

[63] Continuation-in-part of Ser. No. 698,304, May 10, 1991, abandoned.

[51] Int. Cl.⁵ .............................................. A61N 1/18
[52] U.S. Cl. .................................................. 128/419 S
[58] Field of Search ..................... 128/419 S, 731, 732, 128/733

[56] References Cited

U.S. PATENT DOCUMENTS

| | | | |
|---|---|---|---|
| 4,184,485 | 1/1980 | Aguston | 128/732 |
| 4,878,498 | 11/1989 | Abrams et al. | 128/419 S |
| 4,940,058 | 7/1990 | Taff et al. | 128/733 |

Primary Examiner—William E. Kamm
Assistant Examiner—Scott M. Getzow
Attorney, Agent, or Firm—Eliot S. Gerber

[57] ABSTRACT

In electroconvulsive therapy (ECT) the duration of the generated skeletal muscle, heart and brain wave activity during the administration of the electrically induced therapeutic seizures is automatically monitored. The ECT device includes a special purpose electromyograph (EMG) to detect isolated muscle activity and, in one embodiment, an electrocardiograph (ECG) to detect heart-beat intervals, and in another embodiment also includes an electroencephalograph (EEG) system to detect an EEG parameter of the electrically induced EEG seizure. The detected voltage from the EMG, ECG and EEG are converted to digital data and compared to a set of threshold reference values previously obtained from the same patient. The operator is informed by a display, or auditory signal, if the selected parameters have crossed the predetermined threshold reference value and the time period, since termination of the ECT that each parameter has taken to reach the reference value.

30 Claims, 3 Drawing Sheets

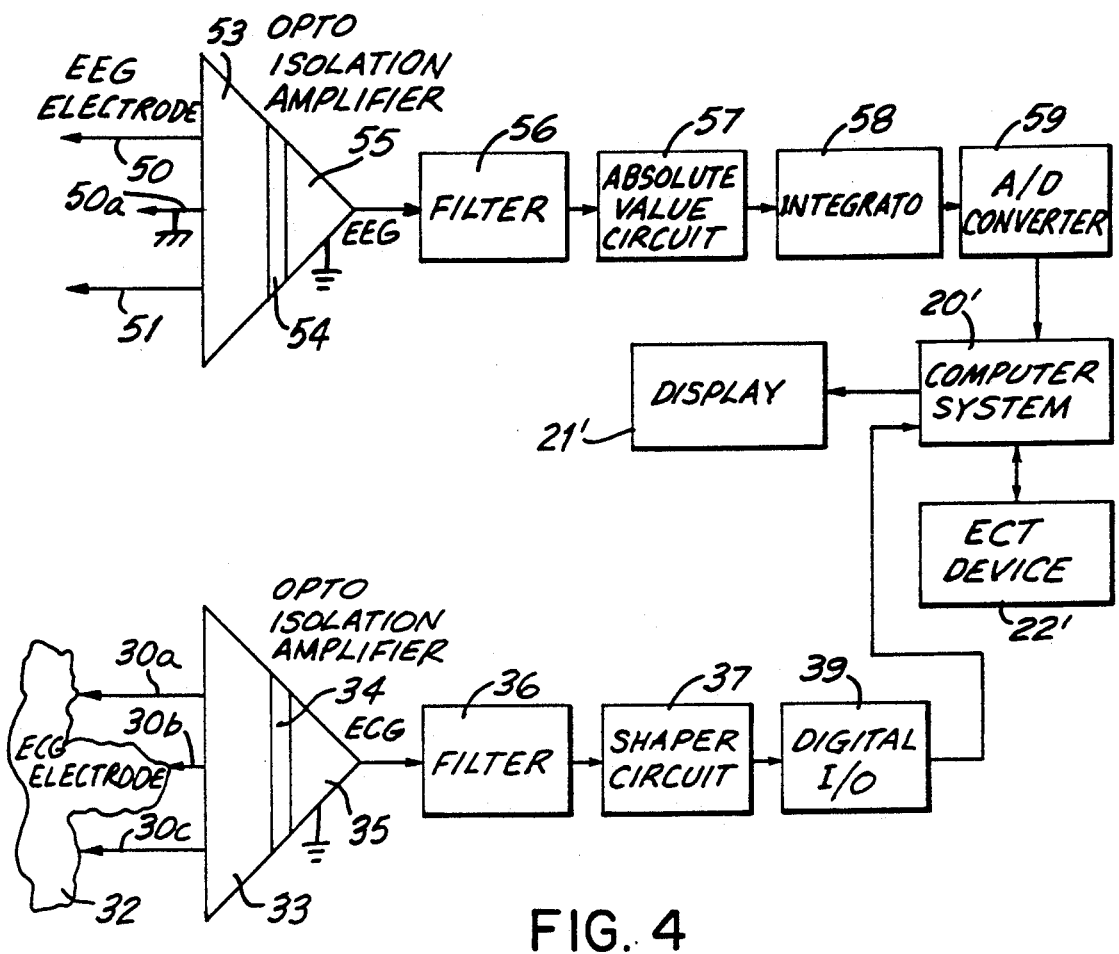
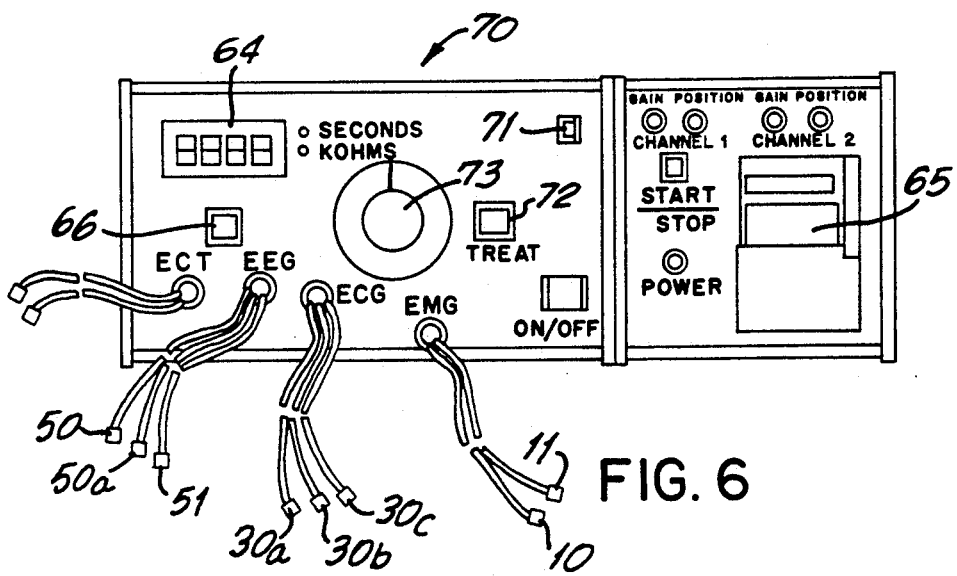

ELECTROCONVULSIVE THERAPY APPARATUS AND METHOD FOR MONITORING PATIENT SEIZURES

This application is a continuation-in-part application partly based upon U.S. patent application Ser. No. 07/698,304, filed May 10, 1991 now abandoned.

BACKGROUND OF THE INVENTION

1. Field of the Invention

The present invention relates to medical apparatus and methods and more particularly to electroconvulsive therapy (ECT) apparatus and methods for automatic monitoring of the duration of patient seizures.

2. Description of the Related Art

In electroconvulsive therapy (ECT) generally two electrodes are applied to the temple of the patient, one on the left and the other on the right side, and a small and carefully controlled electric current is applied for less than ten seconds between the two electrodes. Only a small portion of the current reaches the brain because most is deflected by the skull.

Electroconvulsive therapy ("ECT") may be used to treat major depression. A report of a NIMH panel (National Institute of Mental Health), reported in *Science* (Jun. 28, 1985, pgs. 1510,1511), concluded that "not a single controlled study has shown another form of treatment to be superior to ECT in the short-term management of severe depressions." That article stated that the complication rate is about 1 in 1700 treatments and that severe and prolonged memory loss is extremely rare, and possibly non-existent.

In ECT, the physician determines the length of the applied current, taking into account such factors as the patient's age, size, physical condition and prior ECT. The physician may, with presently available apparatus, reasonably accurately select the desired electrical duration. For example, in the "Thymatron" ECT instrument (TM of Somatics, Inc., Lake Bluff, Illinois) the stimulus may be selected to be a brief series of electrical square waves, providing a constant current of 0.9 amps limited to 450 volts, consisting of 140 bipolar pulses per second of 1 msec width, which is adjustable, by the physician, 0.2-4.0 seconds in duration.

ECT induces an electrical response in the neural tissue of the patient's brain and its therapeutic benefit is primarily due to the induced seizure. That seizure may be displayed on an electroencephalograph (EEG) instrument, using analog printed wavy lines. It presents a pattern similar to a typical epileptic grand mal seizure pattern.

When administering ECT, the physician may monitor the patient to determine the occurrence and duration of the induced seizure (American Psychiatric Association Task Force on ECT Report, Washington, D.C. 1990, pp. 28–29). An electrical stimulus that does not induce a seizure, or induces a seizure of insufficient duration (e.g., less than 20 seconds) is not considered to have sufficient therapeutic effect. If a seizure of sufficient duration is not induced, the treatment may be repeated with a larger electrical dosage, i.e., generally a greater electrical charge, to try to induce a suitable seizure.

In electroconvulsive therapy (ECT) it is desirable that each treatment appears to achieve a definite therapeutic impact. The criteria for apparent effectiveness of the treatment is that muscle (motor) manifestations of the seizure of ECT last for at least 20 seconds and appear generalized through the body. If the seizure is shorter, or the seizure is local rather than generalized, the treatment should generally be repeated, usually with a larger electrical stimulus. A seizure that is unduly long (e.g., longer than 3 or 4 minutes) may cause excessive memory impairment in the patient, or interfere with the patient's orientation to the environment, or require more intensive supervision of the patient during and after the treatment. It is accepted medical practice to immediately terminate such prolonged seizures by administration of suitable intravenous anticonvulsant agents according to the physician's judgment.

Generally, the conventional methods which monitor the electrical activity of the brain during ECT are based on analog EEG technology. For example, an EEG device amplifies the patient's brain waves, filters the amplified brain wave signals to remove muscle artifact and ambient electrical noise, displays the brain wave activity in the form of wavy lines on paper or lines on an oscilloscope screen, or produces similarly fluctuating audible tones played through an audible speaker. The physician determines the occurrence of the seizure by viewing the paper EEG record, oscilloscope display, or hearing the auditory EEG signal. He determines the length of the seizure by interpreting the particular representation of the EEG signal (a spike-like form on an EEG graph) while simultaneously viewing a timepiece. However, the physician's interpretations of the visual, or auditory, EEG signals require familiarity with EEG patterns that occur during ECT. That interpretation is subjective, relies on the attention and experience of the physician, and has been reported in the medical literature to be unreliable (Ries, R. K., *Biol. Psychiat.* 20:94–119, 1985). The physician, to determine the duration of the seizure, must pay attention to the visual, or auditory, representation of the EEG signal, as well as to a separate timepiece, at the same time his attention is required to observe the patient undergoing the seizure.

In the inventors' U.S. Pat. Nos. 4,873,981 and 4,878,498, incorporated by reference herein, the duration of the patient's seizure is automatically monitored. The patient's brain wave activity is amplified by an EEG system, converted to digital data, and compared to the patient's own reference value to determine when a selected EEG parameter has crossed the predetermined reference value ("crossover") and the time which has elapsed from the termination of ECT until the crossover.

It has also been suggested that as an alternative, or as an addition, to the EEG, the patient's muscle activity may be monitored by the physician to determine the end of the seizure, since such ECT-induced seizures provide characteristic involuntary muscle activity. However, generally prior to the ECT the patient will be partly or wholly anesthesized or treated with muscle relaxing pharmacologic agents to obtain anesthesia and prevent bone and muscle injury. Consequently, the patient's muscle activity may be so repressed as to be an unreliable indication of the termination of the seizure. One suggestion, to avoid this problem, is to isolate the monitored muscle group from the muscle relaxing drugs by applying a tourniquet and then for the physician to observe the muscle activity, i.e., a "cuffed limb", see Greenberg, "Detection of prolonged seizures during electroconvulsive therapy; a comparison of electroencephalogram and cuff monitoring", *Convulsive Therapy*, 1:32–37, 1985. However, that method has not been widely adapted, possibly because it requires that physician's attention during a critical period of the ECT. In addition, although seizure-associated muscle activity can be reliably observed by occluding arterial flow to a limb prior to infusion of the muscle paralyzing medication, in many cases seizure activity observable on the EEG has continued long after cessation of observable muscle activity with this "cuffed-limb" method. The "cuffed limb" method cannot describe the quality of generalization of the seizure over the patient's body, because its observation is made only on one limb. It also absorbs staff time, and is unsuitable for patients who are susceptible to osteoporotic bone fractures.

Another alternative or addition to the EEG is the duration of elevation of the heart-beat rate. Such elevation reliably accompanies the seizure activity. The heart-beat rate declines abruptly at the end of the seizure, and the point of greatest descent of this rate consistently marks the end of the seizure.

Generalization of muscle seizure activity over the body does not imply generalization of electrical seizure activity through the brain, which is the goal, because control of muscle activity concerns only a small fraction of the brain. Observation of the EEG, EMG and ECG together describes generalization of electrical seizure activity through the brain. This is because the EEG represents activity in the prefrontal cortex of the brain, the EMG represents activity in the motor area of the brain slightly forward of the middle, and ECG heart rate represents activity in the lower brainstem, which is entirely across the brain from the prefrontal cortex.

SUMMARY OF THE INVENTION

In accordance with the present invention, there is provided an apparatus and method for the automatic monitoring of the duration of the patient's seizure induced during ECT therapy. The automatic procedure obliviates the reliance on the physician's skill and attention and is adapted to reflect the individual condition of each patient at the time of the therapy.

In one embodiment, the electrodes of an electromyograph (EMG) are arranged on a major muscle group on a limb of the patient and pharmological agents are prevented from reaching that limb. The weak analog signals of the EMG (millivolt level) are amplified and converted into digital data. The patient may be tested prior to ECT to provide a threshhold reference level, and then tested during the ECT, or a general threshhold reference level may be used, based upon data obtained from other patients.

The ECT induced seizure causes muscle activity which is reflected in higher time-averaged voltage levels. The seizure is deemed terminated when such levels return to ("crosses") the predetermined threshhold level.

In another embodiment, which may be used along with or as a substitute for the EMG determination, the heart-beat rate is measured, preferably by timing intervals between the R beats. The patient's heart-beat rate just before the ECT stimulus may be the reference threshold level and may be automatically compared with the patient's heart-beat rate after the termination of the ECT current to determine the end of the induced seizure. Alternatively, the end of the induced seizure is recognized as the time of occurrence of the greatest deceleration of the heart-beat.

In another embodiment the EEG measures brain wave power, and displays the results, after the ECT seizure is induced. The total EEG power, or power in one or more frequency bands, such as the Delta band (2.5 Hz to 3.5 Hz) is determined by automatic calculation of the mean integrated voltage times the duration of the ECT induced seizure.

The EEG induced seizure endpoint detection is combined with the EMG induced seizure endpoint detection to provide a "seizure concordance index". The EEG mean integrated voltage of the total power, or power in one or more selected bands, provides a "seizure suppression index", which is the percentage of reduction in EEG power when the induced seizure reaches its endpoint. If the EEG power measurement determines that the induced seizure endpoint has not been reached in a selected time period, for example, 120 seconds, a "seizure duration alert" may be signaled to the operator so that the seizure may be terminated if it exceeds 180 seconds in duration.

The method and system automatically monitors, determines and displays the occurrence, duration, termination, generalization, intensity, coherence, character and quality of the electrically-induced therapeutic seizure of electroconvulsive therapy by electronic processing of EEG along with ECG and/or EMG (electrical voltages generated by the body). The electrical voltages may be determined by their amplitudes, integrated amplitudes frequencies, and time between repeated patterns of voltages generated by the heart, the muscles, and the brain. The results of the determination are generated, for example, as a signal by a loudspeaker or a display such as an alphanumeric display via lights, liquid crystals, paper, or a cathode-ray tube. The display indicates that the selected parameter has reached a predetermined value (threshhold level) which is selected to discriminate the onset, termination, generalization, intensity, coherence, character and quality of the seizure activity.

OBJECTIVES OF THE INVENTION

It is an objective of the prevent invention to provide an apparatus and method in ECT which employs digital computer-based algorithms to determine and display ECT seizure occurrence, endpoint, length, quality, generalization, coherence and intensity.

It is a further objective of the present invention to provide such accurate determinations without the necessity for special medical expertise and familiarity with EEG patterns of ECT seizures, and which decreases the physician's time required for judgments about seizure length and quality.

It is a still further objective of the present invention to provide such an apparatus and method to allow uniformly standardized descriptions of ECT-induced seizure duration, intensity, coherence, generalization and quality; which descriptions are applicable to all patients regardless of their medical condition, It is a further objective of the present invention that the testing procedure be non-invasive.

BRIEF DESCRIPTION OF THE DRAWINGS

Other objectives of the present invention will be apparent from the following detailed description, taken in conjunction with the accompanying drawings.

In the drawings:

FIGS. 4 and 5 are block diagrams of other embodiments of the present invention; and FIG. 6 is a front plan view of the embodiment of FIG. 5.

DETAILED DESCRIPTION OF THE INVENTION

The apparatus and method automatically, continuously and repeatedly measures one or more particular aspects of the ECG, EMG, EEG, alone or in combination, and compares these measurements to the patient's pre-ECT level to determine the occurrence, duration, termination, generalization, intensity, coherence, character, and quality of the electrically-induced therapeutic seizure of electroconvulsive therapy.

Figure 1:
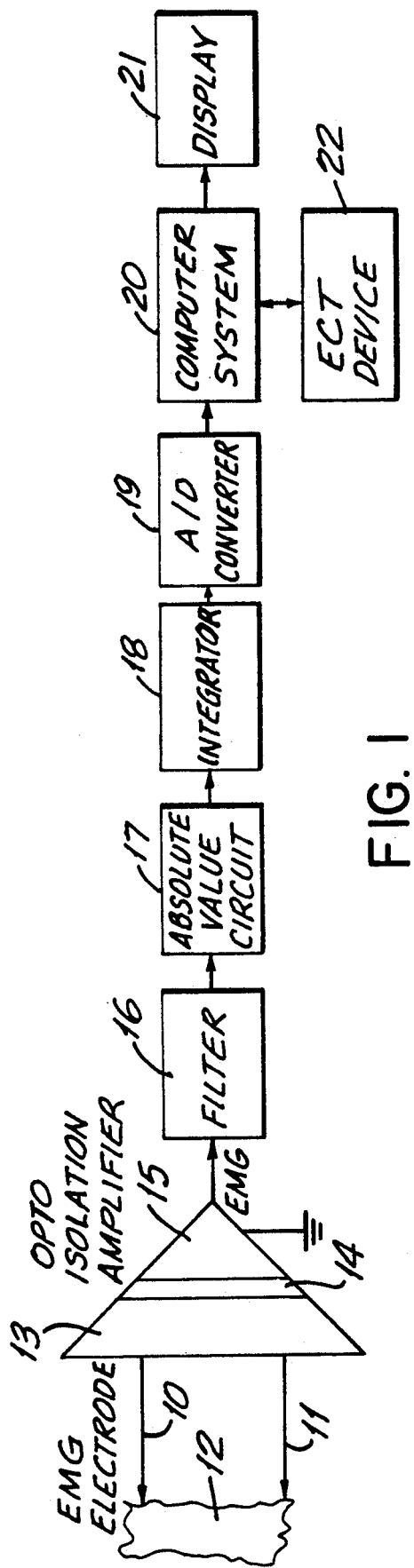
FIG. 1 is a block diagram of the first embodiment of the present invention.

In the first embodiment shown in FIG. 1, the EMG signal is sensed via two disposable or reusable electrodes 10 and 11 pasted on a limb 12 of the patient whose arteries have been occluded by external pressure from a tourniquet or sphygmomanometer (air expandable cuff) to exclude muscle relaxant drug and its effects from the distal musculature (the muscles of the limb). The electrodes 10 and 11 are pasted over a major muscle group. The signals from electrodes i and i? are amplified with a differential instrumentation amplifier 13. For patient safety the signal is isolated with optoelectronic isolator 14. The EMG signal is then further amplified by amplifier 15 and its frequency is limited with a 2-100 Hz filter 16. The signal is then passed through an absolute value circuit 17 and an integrator 18 to provide the mean value of the EMG. The mean analog value is then sampled and digitized by the analog-digital (A/D) converter 19 at the millisecond rate (1000 samples/sec./channel) to provide digital data. The computer system 20, connected to A/D converter 19, calculates the time of the steepest drop in the EMG voltage. The baseline (pre-stimulus) computed EMG voltage may be determined, e.g., as the average wide-band integrated voltage taken over 5 seconds; alternatively a reference level based on data obtained from other patients may be used to determine the baseline (reference). The computer system 20 may be a single chip 8 or 16 bit microcomputer (microprocessor), for example, a 16-bit HD68000 available from Hitachi (a NMOS chip available in a DC-64 package).

When the collection of the baseline voltage measurement has been accomplished, the operator is signaled via an electronic display 21. He may then deliver the ECT electrical signals by triggering a switch on the ECT device 22. Periodic repeated sampling (e.g., at least once per second, but typically 20 to 50 times per second) of the post-stimulus electronically-processed EMG voltage is automatically begun when the ECT electrical stimulus has concluded or the halt of the ECT stimulus, via microcomputer 20, starts the EMG sampling. The electronically-processed EMG voltage of each post-stimulus sample is compared to the pre-stimulus mean value or other selected reference value. When a measurement occurs below a predetermined reference threshold (e.g., twice the baseline activity), the monitoring procedure terminates and the operator is signaled via an electronic alphanumeric digital display 21, or alternatively an oscilloscope screen or a print-out on a moving paper record. The operator is advised that the predetermined threshhold has been crossed and of the time elapsed between the end of the ECT electrical stimulus and the crossing of the threshhold, i.e., that the seizure has ended and how long it lasted. If the post-stimulus processed voltage measurement fails to exceed a particular minimum amount (e.g., 5 times baseline), the procedure is terminated and the operator is signaled, on display 21 or other display, that there was no evidence of seizure.

ECG signals are electrical potential traces or waves accompanied by the contraction of the different cavities of the heart. They are an important aid in the study of heart activity. A typical ECG signal, produced by placing electrodes against the patient's skin, includes P, Q, R, S and T waves, which are all easily discernable by existing equipment. Thus these ECG signals are commonly measured by a pen on paper at frequencies of 0-50 Hz, this frequency range being normally sufficient for discerning such waves since the heartbeat rate is approximately 1 per second, and the rise time of these waves is in the order of 0.1 second.

Figure 3:
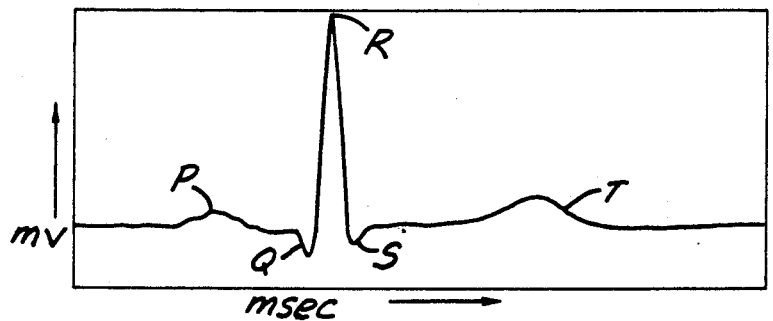
FIG. 3 is a diagram of heart beat waveforms.

A typical heart beat, as shown in FIG. 3, consists of an initial flat isoelectric portion; a "P" wave, a negative "Q"wave; an "R" wave whose leading-upward slope is the depolarization wave and whose lagging-downward slop is the repolarization wave; a negative "S" wave; the "S-T" segment between the S and T waves; the "T" wave, and sometimes a final small "U" wave. Preferably the heart rate is determined by the time interval between R wave peaks, although alternatively other portions of the heart waves may be detected and used to determine the rate. Preferably the heart beat rate is detected by at least 3 electrodes, although the conventional 12-electrode system may be used.

Figure 2:
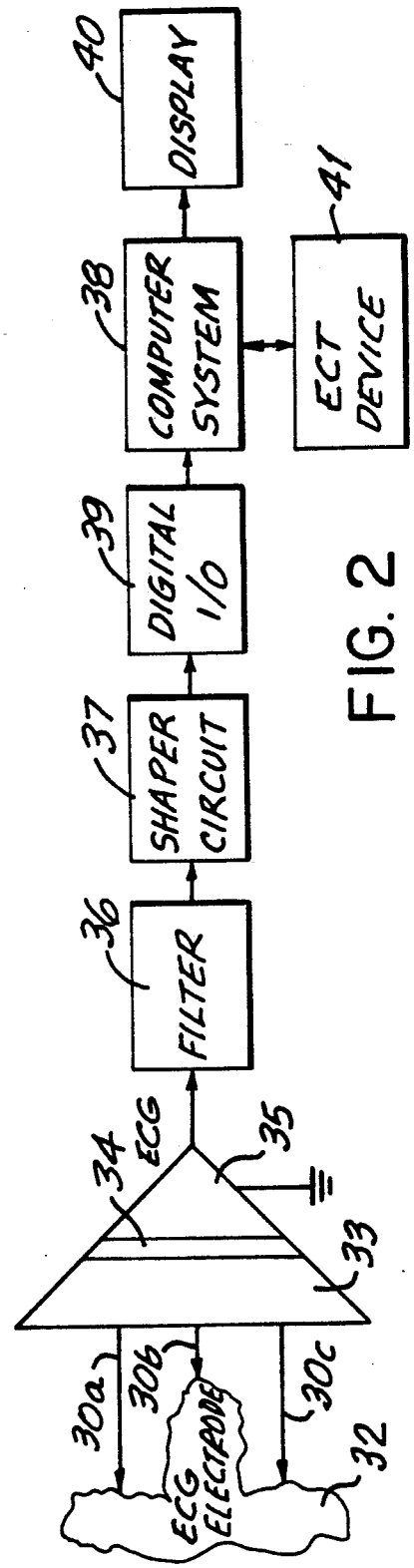
FIG. 2 is a block diagram of the second embodiment of the present invention.

In the second embodiment, shown in FIG. 2, the ECG signal (electrocardiograph), which detects heart activity, is sensed via three disposable or reusable electrodes 30a, 30b and 30c pasted on the chest 32 of the patient. The ECG signal is amplified with a low-noise differential amplifier 33 (less than one microvolt of noise) having a band width of 0-300 Hz. For patient safety the signal is isolated with optoelectronic isolator 34. The ECG signal is then further amplified by amplifier 35 and its frequency is then limited with a 2-50 Hz filter 36. The signal is then passed through a shaper circuit 37 which detects the R-wave of the ECG and provides a square wave output compatible with detection by the digital circuitry of the computer system 38. The pulse output of shaper circuit 37 is connected to a digital input-output circuit 39 which provides a digital interrupt signal with every heartbeat, i.e., it is a rate detector. The heart rate is determined beat-to-beat by timing the interval between successive R-waves. The system will calculate the time of the steepest drop in the heart rate. The pre-stimulus (baseline) frequency is determined over a 5-second period as a point of reference. After the operator delivers the ECT electrical stimulus, by triggering a treatment switch on the ECT device 41, the heart rate is followed. It customarily accelerates, plateaus, and then decelerates, first abruptly and then slowly. The time of occurrence of greatest deceleration is identified by comparing the beat-to-beat changes in chart rate. This time is then reported to the operator via the electronic alphanumeric display 40, or alternatively via a moving paper record. If the heart rate fails to accelerate by at least 5% over prestimulus (baseline) frequency after the stimulus, the operator is informed that there was no observed effect on the heart rate.

In the third embodiment, shown in FIG. 4, the ECG signal is determined and processed as in the second embodiment and simultaneously the EEG signal is determined and processed as in U.S. Pat. Nos. 4,777,952;

4,873,981 and 4,878,498. The ECG signal provides the heart rate-derived seizure duration; the EEG provides the cerebral seizure duration relative to the location of the EEG electrodes placed on the head. A specified numerical function of these two measures of seizure duration, preferably the arithmetic difference, is computed by computer system 20' and reported as a reflection of the quality of generalization of the seizure; e.g., the larger the difference, the smaller is the quality of generalization, on the display 21''. Likewise, and in place of the seizure lengths determined by ECG and EEG, the seizure lengths as determined by ECG and EMG can be combined, or the seizure lengths determined by EEG and EMG can be combined.

Figure 5:
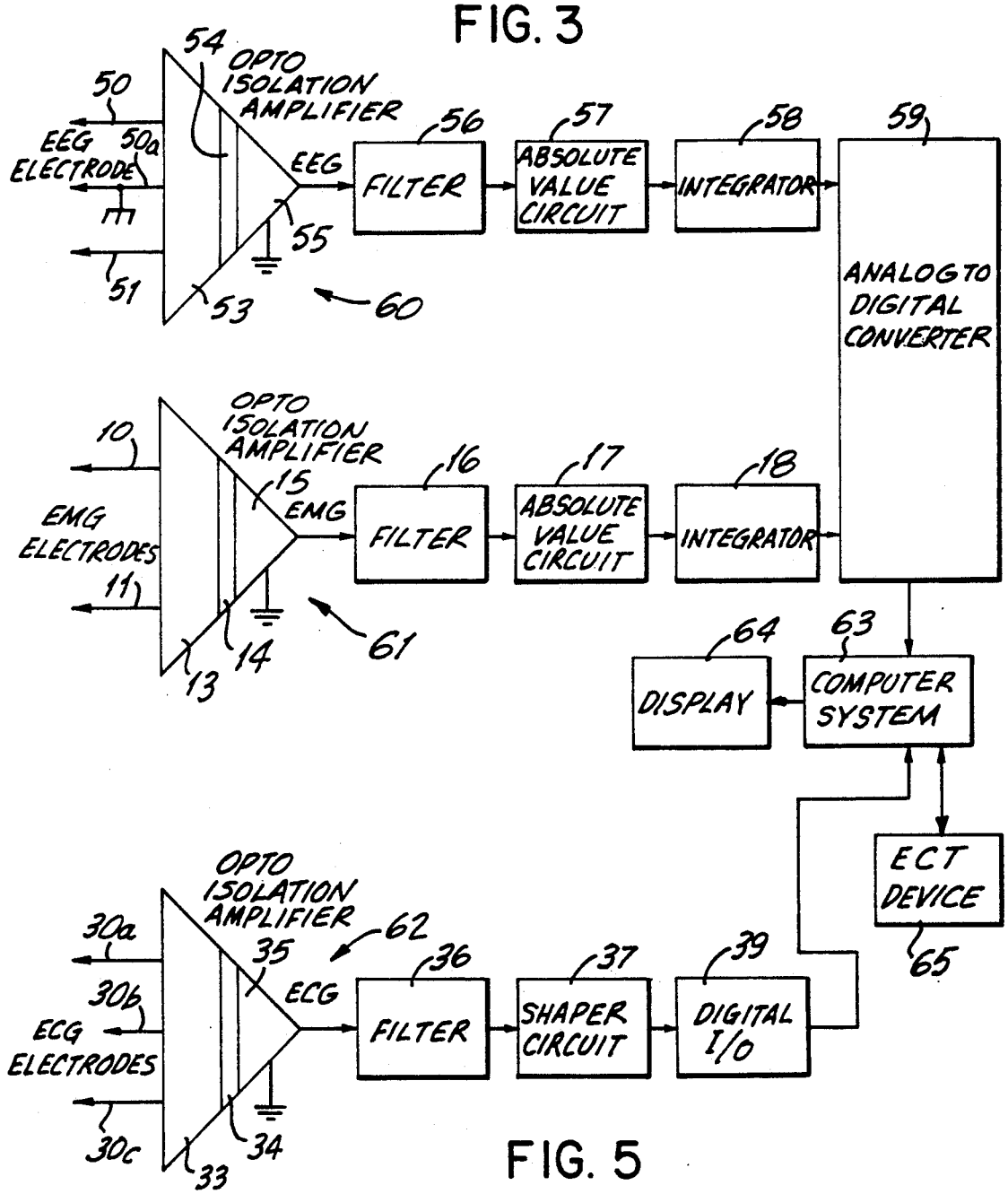

In the fourth embodiment, shown in FIG. 5, the EEG signal is determined from two disposable or reuseable scalp electrodes 50 and 51 pasted over sites on the head 52, e.g., on the forehead, typically above the eyes, or over the mastoid processes, or above one eye and over one mastoid process. The EEG signal can alternatively be sensed directly from the treatment electrodes if they are placed over the temple or on the forehead. The EEG signal is then amplified with a differential instrumentation amplifier 53. To minimize unintended current exposure for patient safety, the signal is isolated with optoelectronic isolator 54. The EEG signal is then further amplified by amplifier 55 and its frequency is limited with a 2-25 Hz filter 56. The signal is then passed through an absolute value circuit 57 and an integrator 58 to provide the mean value of the EEG. The mean analog value is then sampled and digitized by an analog-to-signal (A/D) converter 59. The system will calculate the time of the steepest drop in the EEG voltage.

The patient's brain waves, as detected by the EEG electrodes 50, 50a, 51 and amplified and digitized by the EEG system, shown in FIG. 5, may be used to provide additional information to the operator. The EEG signal may be divided, by filters, into selected frequency bands within the 2-25 Hz band of filter 56. The Delta band is 2-3.5 Hz and, according to published studies, constitutes most of the brain wave energy generated during the ECT-induced seizure and is considered to be the seizure's primary therapeutic component. The Theta band is 3.5-7.5 Hz, the Alpha band is 7.5-12.5 Hz and the lower portion of the Beta band is 12.5-25 Hz. Preferably the "absolute power" in the Delta band (2-3.5 Hz) is measured, although alternatively or in addition absolute power across the entire 2-25 Hz spectrum may be measured or absolute power in other bands may be measured. The "absolute power" is the mean integrated voltage in the selected band taken over the duration of the ECT-induced seizure. The absolute power in the Delta band is called the "Delta Energy Index". The "energy" is power times the number of seconds. That index is displayed to the operator at the end of the ECT-induced seizure and printed in an end-of-treatment report. Alternatively, a "Total Energy Index" may be obtained, displayed and printed-out, based upon the absolute power measured by the mean integrated voltage across the entire band 2-25 Hz and taken over the duration of the ECT-induced seizure.

The EEG digitized data provides the basis for a "Seizure Concordance Index" which is the percentage of concordance (between 0% and 100%) between the EEG and EMG measurements of ECT-induced seizure duration. The EMG and EEG seizure endpoint detectors automatically detect the seizure's endpoint. For example, if the two (EEG and EMG) endpoint detectors agree exactly, then the Seizure Concordance Index is 100%. If they disagree entirely, i.e., one detects an endpoint and the other does not, the index is 0%. If one endpoint detection is at 180 seconds and the other at 90 seconds, then the index is 50%.

Because the EEG and EMG seizure activity each reflect cortical discharges in different parts of the brain, the concordance of their relative seizure durations reflects the intensity or degree of generalization of the ECT-induced seizure throughout the brain, which is believed to directly correlate with the therapeutic impact of the ECT-induced seizure.

The EEG data may be used to compute and display a "Seizure Suppression Index" under a suitable computer software program. That index is the percentage of reduction in the EEG power (mean integrated voltage) which occurs when the ECT-induced seizure reaches its endpoint. The percentage range is 0% to 100% and the seizure endpoint may be determined as described above. Because the degree of postictal flattening, or suppression, is likely to reflect the extent of EEG seizure generalization throughout the brain, the seizure suppression index would document another and different aspect of the therapeutic impact of the ECT-induced seizure.

In addition, a "Seizure Duration Alert" automatically signals the operator (e.g., via beeping tone or flashing light) when 120 post-stimulus seconds had elapsed and automatic detection of the EEG seizure endpoint had not yet been received. Most EEG seizures last less than 120 seconds and there is no relation between seizure duration and therapeutic impact. However, there is a clear and direct relation between seizure duration and undesirable side-effects, especially for seizures prolonged beyond 180 seconds. Consequently, most clinicians terminate ECT-induced seizures lasting longer than 180 seconds. The "Seizure Duration Alert" warns the operator that he should consider terminating the seizure unless it has spontaneously terminated before an additional 60 seconds expires. Alternatively, the operator could simply be signaled at 120 post-stimulus seconds, even without the automatic EEG monitor enabled. In this case, the 120-second warning serves as an alerting timer to remind the operator that a potentially critical post-stimulus time (e.g., 180 seconds) was approaching, so that any necessary appropriate action (e.g. external termination of the seizure by anticonvulsant agents) could be taken. The EEG monitor may be automatically terminated and a printed end-of-treatment report is generated when a specified interval (e.g., 10 seconds) had elapsed after automatic EEG seizure endpoint detection had occurred.

This fourth embodiment provides three independent channels of digital data, channel 60 for EEG, channel 61 for EMG, and channel 62 for ECG. Each channel 60-62 is connected to the computer system 63 and presents digital data to the system 63, as in the prior embodiments. The computer system 63 controls ECT device 65 and performs analysis on each channel (i.e., on the EEG, ECG and EMG) and then combines their comparisons of the first and second sets of digital data to present a unified determination which is displayed on the display 64.

In the fifth embodiment (not shown) the EEG signal is processed as in the fourth embodiment, except that two pairs of electrodes are placed over mirror-image sites on both left and right sides of the head, e.g., above both eyes, over both mastoid processes, or from two treatment electrodes placed bifrontally or bifrontotemporally. The coherence of the EEG signal, which is a comparison of EEG signals on the right and left sides of the head, is measured, ongoing, beginning 5 seconds after the end of the ECT stimulus. An abrupt reduction in coherence signals the end of the seizure. The time-integrated amplitude of coherence until the end of the seizure reflects the quality of the seizure.

As shown in FIG. 6, the device 70 includes four conductive EEG electrodes 50, 50a and 51, two conductive EMG electrodes 10 and 11, and three conductive ECG electrodes 30a, 30b and 30c, all of which are removably applied to the skin of the patient. The minimum number of electrodes required for each of the EEG, EMG or ECG is two plus one ground electrode for the system, i.e., seven electrodes; and determination of EEG coherence requires two additional electrodes, for a total of nine. The electrode impedance is tested by the test button 6 and the impedances shown on display 64. The baseline (reference) of the EEG, EMG and ECG may be obtained by pushing the baseline button 71. Preferably the baseline (first set of digital data) for the EEG, EMG and ECG is obtained by measuring the patient twice prior to ECT, and averaging the data from both tests. The ECT treatment is started by pushing "treat" button 72 and the time for the treatment is selected by adjustable timer 73. As in the other embodiments, the elapsed time (from end of treatment to termination of seizure) is measured by the computer system and is shown by LED display 64 and printed out on thermal printer 65. The computer system compares the respective first and second sets of digital data (for the EEG, EMG and ECG) and combines their test results, for example, by obtaining the mean, to obtain a combined determination of the termination of the seizure. When the ECT stimulus ends, the monitoring is automatically started, i.e., the computer system controls the timing of the ECT treatment and the monitoring of the seizure, to produce second sets of digital data for the EEG, EMG and ECG. As in the other embodiments, the seizure monitoring starts 0 to 30 seconds after the end of the ECT stimulus.

We claim:

1. A method in electroconvulsive therapy (ECT) to monitor the termination of an induced seizure in a patient, the method including the steps of:
    (a) selecting a major muscle group of the patient and isolating the muscle group from effects of muscle relaxing pharmacological agents;
    (b) detecting the muscle activity of the muscle group prior to the ECT by amplifying the electrical signals from the muscle group to detect EMG signals, converting the EMG signals into a first set of EMG digital data, setting an established EMG reference voltage for the EMG signals based upon the first set of EMG digital data, and storing in system digital computer memory the established EMG reference voltage;
    (c) employing an ECT device, removably securing a plurality of electrodes of the ECT device on the head of the patient and applying electricity through the electrodes in an electroconvulsive therapy session to induce seizure;
    (d) in the range of less than 30.0 seconds immediately following termination of the application of electricity to induce the seizure by the ECT device, commencing detecting the muscle activity of the major muscle group of the patient by amplification of the electrical signals from the patient's muscle group using the EMG device and removable electrodes and converting the amplified EMG signals into a second set of digital EMG data in order to commence the monitoring of the termination of the seizure;
    (e) automatically determining, by use of the digital computer system, the termination of seizure as indicated by the monitored EMG signals declining to the established EMG reference voltage by a comparison of the established EMG reference voltage with the second set of digital EMG data; and
    (f) displaying the results of said comparison as indicating said termination of seizure.

2. A method in electroconvulsive therapy as in claim 1, including the step of measuring and displaying an elapsed time from the commencement of said monitoring until the termination of seizure.

3. A method in electroconvulsive therapy as in claim 1 including displaying the lack of a seizure by the monitored EMG signals not increasing to the established EMG reference voltage within a selected time period.

4. A method in electroconvulsive therapy as in claim 1 wherein the first and second sets of data are integrated voltages over a selected time period in the range of 0.5-3 seconds.

5. A method in electroconvulsive therapy as in claim 1 including the step of establishing the established EMG reference voltage prior to said ECT by measuring said muscle activity during at least two selected time periods, during which said periods the muscle activity is within a selected percentage of one period compared to another period, and averaging said muscle activity over said periods.

6. A method in electroconvulsive therapy as in claim 1 including the additional steps of:
    (a) detecting the brain wave activity of the patient prior to the ECT by amplifying the electrical signals from the brain using an electroencephalographic (EEG) device having electrodes removably attached to the head of the patient to detect EEG signals, converting the EEG signals into a first set of EEG data and setting an established EEG reference voltage based on the first set of EEG data, and storing in system computer memory the established EEG reference voltage;
    (b) in the range of less than 30 seconds immediately following termination of the application of electricity to induce the seizure by the ECT device, commencing detecting the brain wave activity of the patient by amplification of the electrical signals from the brain using the EEG device and removable electrodes and converting the amplified EEG signals into a second set of EEG data to commence the monitoring of the termination of the seizure;
    (c) automatically analyzing the termination of seizure as indicated by the monitored EEG signals declining to the established EEG reference by a comparison, using the digital computer system, of the established EEG reference voltage with the second set of EEG data;
    (d) combining the EEG comparison with the EMG comparison in the computer system to provide a combined EMG and EEG determination of the termination and generalization of seizure; and
    (e) displaying the results of said combined determinations indicating said termination of seizure.

7. A method in electroconvulsive therapy as in claim 6 wherein EEG electrodes are applied to the head of the patient on opposite sides of the head and, by changes in EEG coherences, seizure onset and termination are thereby detected.

8. A method in electroconvulsive therapy as in claim 1 wherein the patient has a brain having portions susceptible to different cortical discharges, including the additional steps of:
   (a) detecting the brain wave activity of the patient prior to the ECT by amplifying the electrical signals from the brain using an electroencephalographic (EEG) device having electrodes removably attached to the head of the patient to detect EEG signals, converting the EEG signals into a first set of data, setting an established EEG reference based on the first set of EEG data, storing in system computer memory the established EEG reference;
   (b) in the range of less than 30 seconds immediately following termination of the application of electricity to induce the seizure by the ECT device, commencing detecting the brain wave activity of the patient by amplification of the electrical signals from the brain using the EEG device and removably electrodes and converting the amplified EEG signals into a second set of EEG data;
   (c) automatically, in a digital computer system, analyzing the termination of seizure as indicated by the monitored EEG signals declining to the established EEG reference by a comparison of the established EEG references with the second set of EEG data;
   (d) comparing the EEG termination of seizure comparison with the EMG termination of seizure comparison in the digital computer system to provide a seizure concordance index reflecting cortical discharges in different parts of the brain; and
   (e) displaying the seizure concordance index.

9. A method in electroconvulsive therapy as in claim 1 including the steps of:
   (a) detecting the brain wave activity of the patient prior to the ECT by amplifying the electrical signals from the brain using an electroencephalographic (EEG) device having electrodes removably attached to the head of the patient to detect EEG signals, converting the EEG signals into a first set of EEG data, setting an established EEG reference based on the first set of EEG data, storing in system computer memory the established EEG reference;
   (b) in the range of less than 30 seconds immediately following termination of the application of electricity to induce the seizure by the ECT device, commencing detecting the brain wave activity of the patient by amplification of the electrical signals from the brain using the EEG device and removable electrodes and converting the amplified EEG signals into a second set of EEG data to commence the monitoring of the termination of the seizure;
   (c) automatically in a digital computing system determining the termination of seizure as indicated by the monitored EEG signals declining to the established EEG reference by a comparison of the established EEG reference with the second set of EEG data;
   (d) in the range of less than 30 seconds immediately following termination of the application of electricity to induce the seizure by the ECT device, measuring the power of the brain wave activity of the patient by amplification of the electrical signals from the brain using the EEG device and removable electrodes, and automatically in the digital computer system computing an energy index based upon the multiplication product of the EEG power and the total seizure duration; and
   (e) displaying the energy index and the results of the determination of termination of seizure.

10. A method in electroconvulsive therapy as in claim 9 wherein the energy index is a delta energy index based upon absolute power measured in the delta band.

11. A method in electroconvulsive therapy as in claim 9 wherein the energy index is a total energy index based upon absolute power measured across the entire band of 2–25 Hz.

12. A method in electroconvulsive therapy as in claim 9 wherein a seizure suppression index is automatically computed and displayed, said seizure suppression index being based upon the percentage of reduction in the EEG power at the endpoint of the induced seizure.

13. A method in electroconvulsive therapy (ECT) to monitor the termination of an induced seizure in a patient, the method including the steps of:
   (a) detecting the heartbeat rate of the patient prior to the ECT by amplifying the electrical signals from the heart using an electrocardiograph ECG device having electrodes removably attached to the skin of the patient to detect ECG signals, converting the ECG heartbeat rate signals into a first set of ECT heartbeat rate digital data, storing in system digital computer memory the first set of ECG digital data and setting an established ECG heartbeat rate reference based on said first set of ECG heartbeat rate digital data;
   (b) employing an ECT device, removably securing a plurality of electrodes of the ECT device on the head of the patient and applying electricity through the electrodes in an electroconvulsive therapy session to induce seizure;
   (c) in the range of less than 30 seconds immediately following termination of the application of electricity by the ECT device to induce the seizure, commencing monitoring the heartbeat rate of the patient by amplification of the electrical signals from the heart using the ECG device and removable electrodes and converting the amplified ECG signals into a second set of heartbeat rate digital data in order to commence the monitoring of the termination of the seizure;
   (d) automatically determining the termination of seizure as indicated by the monitored ECG heartbeat rate signals declining to the established reference by a comparison, using the digital computer system, of the established ECG heartbeat rate reference with the second set of ECG digital data; and
   (e) displaying the results of said comparison as indicating said termination of seizure.

14. A method in electroconvulsive therapy as in claim 13, including the step of measuring and displaying an elapsed time from the commencement of said monitoring until said termination of seizure.

15. A method in electroconvulsive therapy as in claim 13 including displaying the lack of a seizure by the monitored ECG signals not increasing to the established ECG reference within a selected time period.

16. A method in electroconvulsive therapy as in claim 13 wherein two paris of detecting EEG electrodes are applied to the head of the patient on opposite sides of the head and changes in EEG coherence seizure onset and termination are thereby detected.

17. A method of electroconvulsive therapy as in claim 13 including the step of establishing the established ECG reference prior to said ECT by measuring said heartbeat rate during at least two selected time periods, during which said periods the heart rate is within the selected percentage of one period compared to another period, and averaging said heart rate over said periods.

18. A method in electroconvulsive therapy (ECT) as in claim 13 including the additional steps of:
 (a) detecting the brain wave activity of the patient prior to the ECT by amplifying the electrical signals from the brain using an electroencephalographic (EEG) device having electrodes removably attached to the head of the patient to detect EEG signals, converting the EEG signals into a first set of EEG data, setting an established EEG reference voltage based on the first set of EEG data; storing in system computer memory the established EEG reference voltage;
 (b) in the range of less than 30 second immediately following termination of the application of electricity to induce the seizure by the ECT device, commencing detecting the brain wave activity of the patient, by amplification of the electrical signals from the brain using the EEG device and removable electrodes and converting the amplified EEG signals into a second set of EEG data to commence the monitoring of the termination of the seizure;
 (c) automatically analyzing the termination of seizure as determined by the monitored EEG signal declining to the established EEG reference by comparison using the computer system of the established EEG reference voltage with the second set of EEG data;
 (d) combining the EEG analysis with the ECG determination in the computer system to provide a combined ECG and EEG determination of the termination and generalization of seizure; and
 (e) displaying the results of said combined determination as indicating said termination of seizure.

19. A method in electroconvulsive therapy (ECT) to monitor the termination of an induced seizure in a patient, the method including the steps of:
 (a) selecting a major muscle group of the patient and isolating the muscle group from the effects of muscle relaxing pharmacological agents;
 (b) detecting muscle activity of the muscle group prior to the ECT by amplifying the electrical signals from the muscle group using an electromyograph (EMG) device having electrodes removably attached to the muscle group to detect EMG signals, converting the EMG signals into a first set of EMG digital data, setting an established EMG reference voltage based on the first set of EMG digital data, storing in system digital computer memory the established EMG reference voltage;
 (c) detecting the heartbeat rate of the patient prior to the ECT by amplifying the electrical signals from the heart using an electrocardiograph (ECG) device having electrodes removably attached to the skin of the patient to detect ECG signals, converting the ECG signals into a first set of ECG heartbeat rate digital data, setting an established heartbeat rate ECG reference based on the first set of ECG heartbeat rate digital data; and storing in system digital computer memory the established ECG heartbeat rate reference;
 (d) detecting the brain wave activity of the patient prior to the ECT by amplifying the electrical signals from the brain using an electroencephalographic (EEG) device having electrodes removably attached to the head of the patient to detect EEG signals, converting the EEG signals into a first set of EEG digital data, and setting an established EEG reference voltage based on the first set of EEG digital data, and storing in system digital computer memory the established EEG reference voltage;
 (e) employing an ECT device, removably securing a plurality of electrodes of the ECT device on the head of the patient and applying electricity through the electrodes in an electroconvulsive therapy session to induce seizure;
 (f) commencing in the range of less than 30.0 seconds immediately following termination of the application of electricity to induce the seizure by the ECT device,
  (i) detecting the muscle activity of the major muscle group of the patient by amplification of the electrical signals from the muscle group using the EMG device and removable electrodes and converting the amplified EMG signals into a second set of EMG digital data;
  (ii) monitoring the heart beat rate of the patient by amplification of the electrical signals from the heart using the ECG device and removable electrodes and converting the amplified ECG signals into a second set of heart beat rate digital data;
  (iii) detecting the brain wave activity of the patient using the EEG device and removable electrodes and converting the amplified EEG signals into a second set of EEG digital data;
 (g) automatically analyzing the termination of seizure as determined by the monitored EEG, ECG and EMG signals approaching the established respective EEG, ECG and EMG references by comparisons using the digital computer system of the established EEG, ECG and EMG references with the second sets of respective EEG, ECG and EMG digital data;
 (h) combining the EEG comparison, and the ECG heart beat comparison and the EMG comparison in the computer system to provide a combined EMG, ECG and EEG determination of the termination of seizure; and
 (i) displaying the results of said combined determination as indicating said termination of seizure.

20. A system in electroconvulsive therapy (ECT) to induce seizure in a patient and monitor the termination of the induced seizure, the system including:
 (a) EMG means for detecting muscle activity of a muscle group prior to the ECT by amplifying electrical signals from the muscle group, said EMG means including an electromyograph (EMG) device and electrodes adapted to be removably attached to the muscle group to produce EMG signals, A/D means for converting the EMG signals into a first set of EMG digital data, and computer means for established and storing in digital computer memory data of an established EMG reference voltage based on the first set of EMG digital data;

(b) ECT means for inducing the seizure including a plurality of electrodes adapted to be removably secured on the head of the patient and means for applying electricity through the electrodes to the patient in an electroconvulsive therapy session to induce seizure;

(c) means for storing a second set of EMG digital data obtained from the EMG means on commencement of the monitoring of the termination of the seizure in the range of less than 30 seconds after ceasing the said application to induce seizure;

(d) means for automatically determining the termination of seizure as determined by the monitored EMG signals declining to the established EMG reference by comparison, using the digital computer system, of the established EMG reference voltage with the second set of digital data; and (e) means for displaying the results of said comparison as indicating said termination of seizure.

21. A system in electroconvulsive therapy as in claim 20, including means for measuring and displaying an elapsed time from the commencement of said monitoring until the said termination of seizure.

22. A system in electroconvulsive therapy as in claim 20 wherein the patient has a brain having portions susceptible to different cortical discharges, including:

(a) EEG means for detecting the brain wave activity of the patient prior to the ECT by amplifying the electrical signals from the brain, said EEG means including an electroencephalographic (EEG) device having electrodes removably attached to the head of the patient to detect EEG signals; means for converting the EEG signals into a first set of data, and setting an established EEG reference based on the first set of EEG data and computer memory means for storing the established EEG reference;

(b) computer memory means for storing a second set of EEG data obtained from the EEG means in the range of less than 30 seconds immediately following termination of the application of electricity to induce the seizure by the ECT device;

(c) digital computer means for automatically analyzing the termination of seizure as indicated by the monitored EEG signals declining to the established EEG reference;

(d) digital computer means for comparing the EEG termination of seizure comparison with the EMG termination of seizure comparison to provide a seizure concordance index reflecting cortical discharges in different parts of the brain; and (e) means for displaying the seizure concordance index.

23. A system in electroconvulsive therapy (ECT) as in claim 20, the system including:

(a) EEG means for detecting the brain wave activity of the patient prior to the ECT by amplifying the electrical signals from the brain, said EEG means including an electroencephalographic (EEG) device having electrodes removably attached to the head of the patient to detect EEG signals, means for converting the EEG signal into a first set of EEG data and for setting an established EEG reference based on the first set of EEG data, and computer memory means for storing the established EEG reference;

(b) computer memory means for storing a second set of EEG data obtained from the EEG means immediately following termination of the application of electricity to induce the seizure by the ECT device;

(c) digital computer means for automatically determining the termination of seizure as indicated by the monitored EEG signals declining to the established EEG reference;

(d) means for measuring the power of the brain wave activity of the patient, by amplification of the electrical signals from the brain using the EEG device and removable electrodes, in the range of less than 30 seconds immediately following termination of the application of electricity to induce the seizure by the ECT device; means for automatically computing an energy index based upon the power measurement; and (e) means for displaying the energy index and results of the determination of termination of seizure.

24. A system in electroconvulsive therapy as in claim 23 wherein the energy index is a delta energy index based upon absolute power measured in the delta band.

25. A system in electroconvulsive therapy as in claim 23 wherein the energy index is a total energy index based upon absolute power measured across the entire band of 2–25 Hz.

26. A system in electroconvulsive therapy as in claim 23 and including means for automatically computing and displaying a seizure suppression index based on the percentage of reduction in the EEG power at the end point of the induced seizure.

27. A system in electroconvulsive therapy (ECT) to induce seizure in a patient and monitor the termination of the induced seizure, the system including:

(a) ECG means for detecting the heart rate of the patient prior to the ECT by amplifying electrical signals from the heart, said ECG means including an electrocardiograph (ECG) device and electrodes adapted to be removably attached to the patient to produce ECG signals, A/D means for converting the ECG signals into a first set of ECG digital data, and computer means for storing in digital computer memory an EEG reference voltage based on the first set of ECG digital data;

(b) ECT means for inducing the seizure including a plurality of electrodes adapted to be removably secured on the head of the patient and means for applying electricity through the electrodes to the patient in an electroconvulsive therapy session to induce seizure;

(c) means for storing a second set of ECG heart beat rate digital data obtained from the ECG means on commencement of the monitoring of the termination of the seizure in the range of 1–30 seconds after ceasing the said application to induce seizure;

(d) means for automatically determining the termination of seizure as determined by the monitored ECG signal compared to the ECG heartbeat rate reference, using the digital computer system; and (e) means for displaying the results of said comparison as indicating said termination of seizure.

28. A system in electroconvulsive therapy as in claim 27, including means for measuring and displaying an elapsed time from the commencement of said monitoring until the said termination of seizure.

29. A system in electroconvulsive therapy (ECT) to induce seizure in a patient by electrical stimulation and monitor the termination of the induced seizure, the system including:

(a) EMG means for detecting muscle activity of a muscle group prior to, during and immediately after the electrical stimulation by amplifying electrical signals from the muscle group, said EMG means including an electromyograph (EMG) device and electrodes adapted to be removably attached to the muscle group to produce EMG signals, A/D means for converting the EMG signals in respective first and second sets of EMG digital data, and computer means for storing in digital computer memory the sets of EMG digital data;

(b) EEG means for detecting the brain wave activity of the patient prior to, during and immediately after the electrical stimulation by amplifying electrical signals from the brain, said EEG means including an electroencephalograph (EEG) device and electrodes adapted to be removably attached to the head of the patient to produce EEG signals, A/D means for converting the EEG signals into respective first and second sets of EEG digital data, and computer means for storing in digital computer memory the sets of EEG digital data;

(c) ECG means for detecting the heart beat rate of the patient prior to, during and immediately after the electrical stimulation by amplifying electrical signals from the heart, said ECG means including an electrocardiograph (ECG) device and electrodes adapted to be removably attached to the skin of the patient to produce ECG signals, A/D means for converting the ECG signals into respective first and second sets of ECG digital data, and computer means for storing in digital computer memory the sets of ECG digital data;

(d) ECT means for inducing the seizure including a plurality of electrodes adapted to be removably secured on the head of the patient and means for applying electrical stimulation through the electrodes to the patient in an electroconvulsive therapy session to induce seizure;

(e) computer means for automatically analyzing the termination of seizure as determined by the monitored EEG, ECG and EMG signals approaching selected respective EEG, ECG and EMG references based on the first sets of respective EEG, ECG and EMG digital data to produce a combined indication of said termination; and (f) display means to display the combined indication of said termination.

30. A system in electroconvulsive therapy as in claim 29, including means of measuring and displaying an elapsed time from the commencement of said monitoring until the said termination of seizure.

* * * * *